(12) United States Patent
Kuwabara

(10) Patent No.: US 6,310,935 B1
(45) Date of Patent: Oct. 30, 2001

(54) FLUORESCENT X-RAY ANALYZER

(75) Inventor: Shoji Kuwabara, Osaka (JP)

(73) Assignee: Shimadzu Corporation (JP)

( * ) Notice: Subject to any disclaimer, the term of this patent is extended or adjusted under 35 U.S.C. 154(b) by 0 days.

(21) Appl. No.: 09/540,929

(22) Filed: Mar. 31, 2000

(30) Foreign Application Priority Data

Jul. 29, 1999 (JP) .................................................. 11-214946

(51) Int. Cl.[7] .................................................. G01N 23/223
(52) U.S. Cl. .................................................. 378/49; 378/45
(58) Field of Search .................................. 378/49, 44, 45, 378/79, 81

(56) References Cited

U.S. PATENT DOCUMENTS

| | | | |
|---|---|---|---|
| 3,663,812 | * 5/1972 | Koenig et al. | 378/49 |
| 4,562,585 | * 12/1985 | Gobel et al. | 378/49 |
| 4,796,284 | * 1/1989 | Jenkins | 378/49 |
| 5,357,551 | * 10/1994 | Bolk et al. | 378/98 |

* cited by examiner

Primary Examiner—David P. Porta
(74) Attorney, Agent, or Firm—Coudert Brothers

(57) ABSTRACT

A fluorescent x-ray analyzer has a light-dispersing crystal and a detector which are rotatable while maintaining a specified angular relationship between them such that fluorescent x-rays from a sample are scanned. A first-order profile and a higher-order profile showing x-ray intensities against scan angle are produced from detection signals from the detector respectively within a different specified range of wavelengths. Data related to ratios between preliminarily measured peak intensities of diffracted beams of first-order and higher-order obtained from a plurality of elements are stored and used to identify peaks in these profiles, if there is a possibility of a peak formed by a first-order spectrum of one element and a higher-order spectrum of another element overlapping each other and the nature and extent of contributions to the peaks in the profiles from the first-order and higher-order spectra are determined.

4 Claims, 8 Drawing Sheets

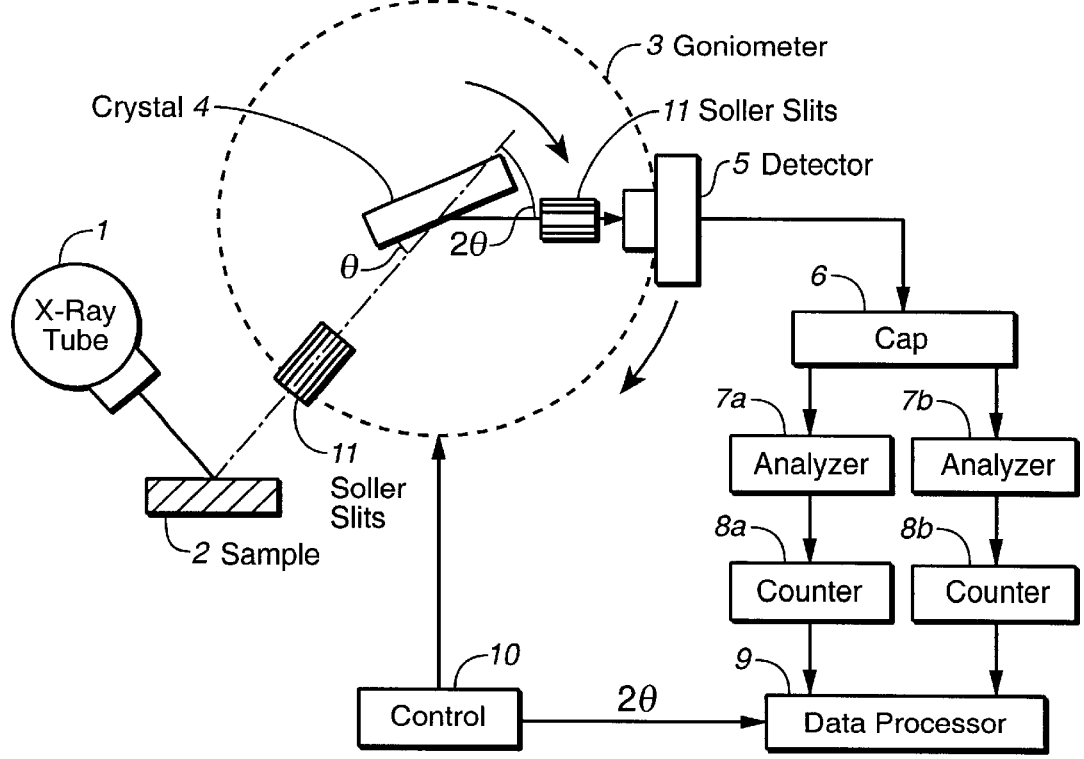
FIG._1

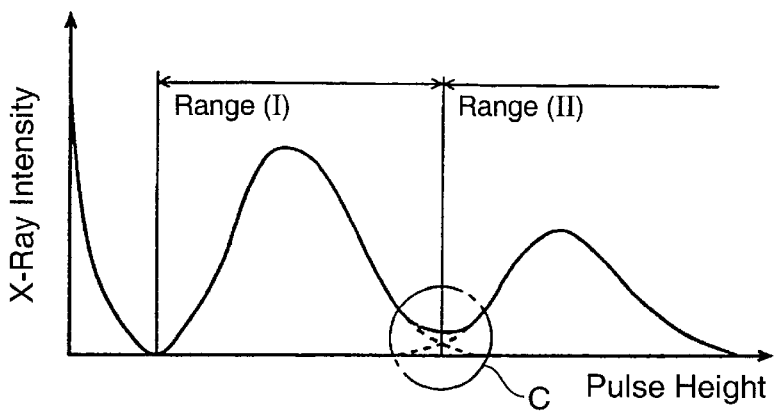
FIG._2A
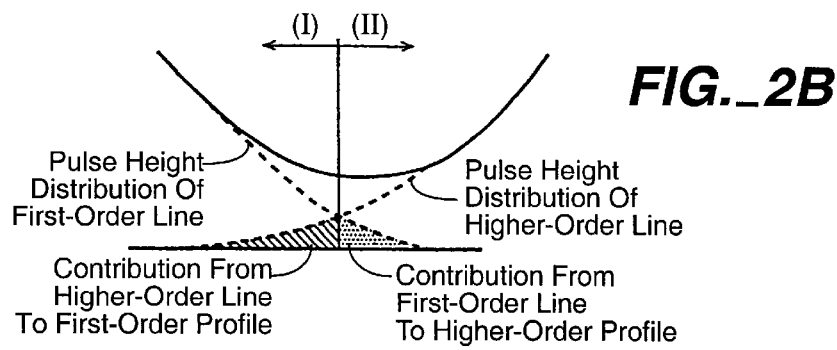
FIG._2B
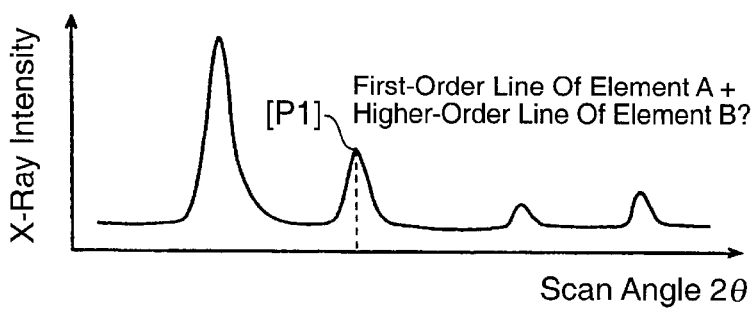
FIG._3A
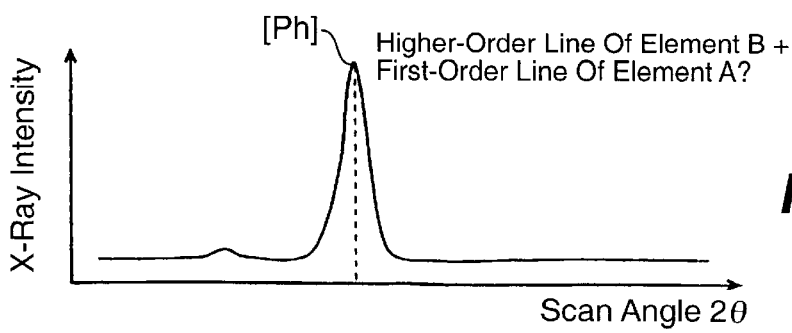
FIG._3B

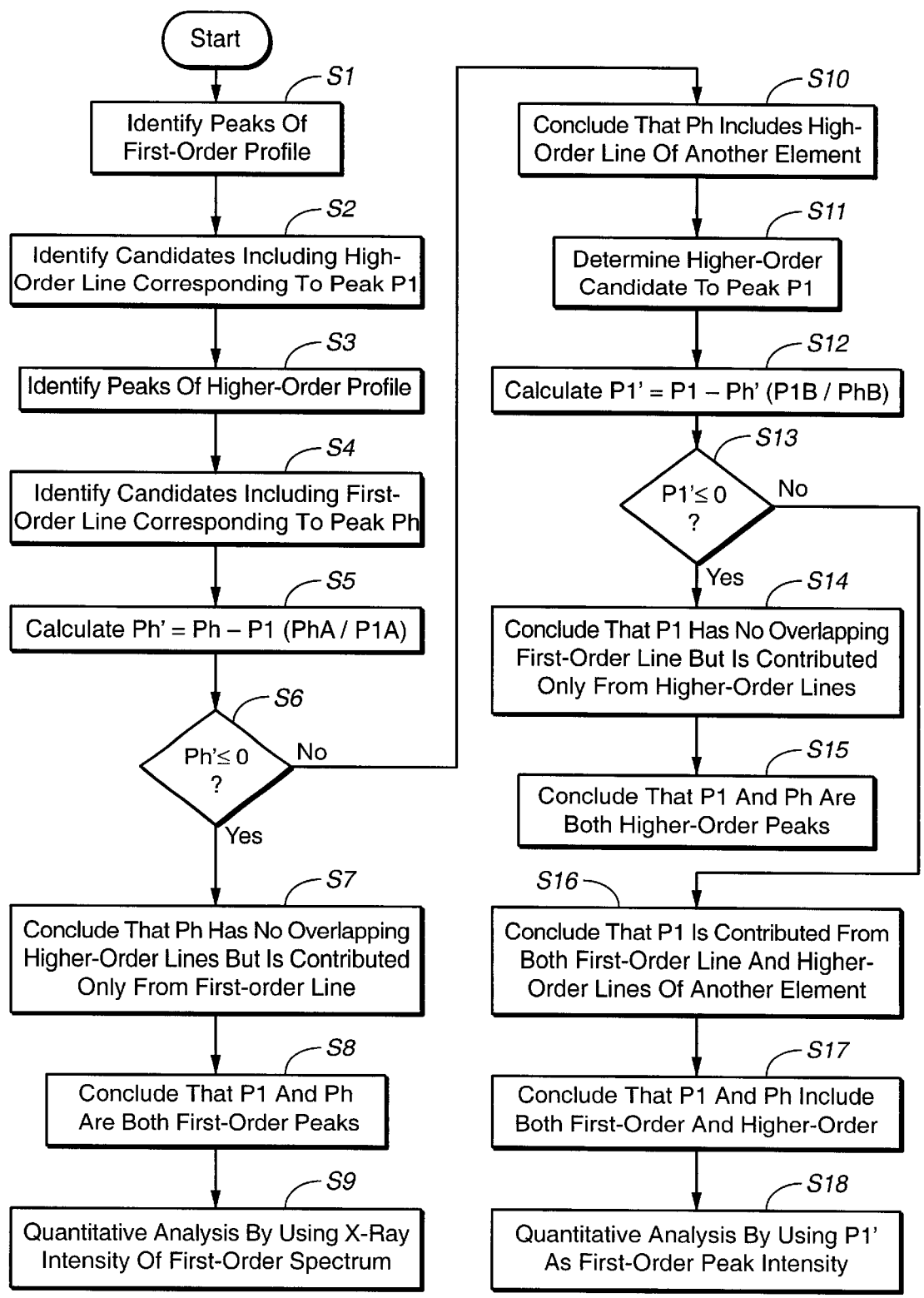
FIG._4

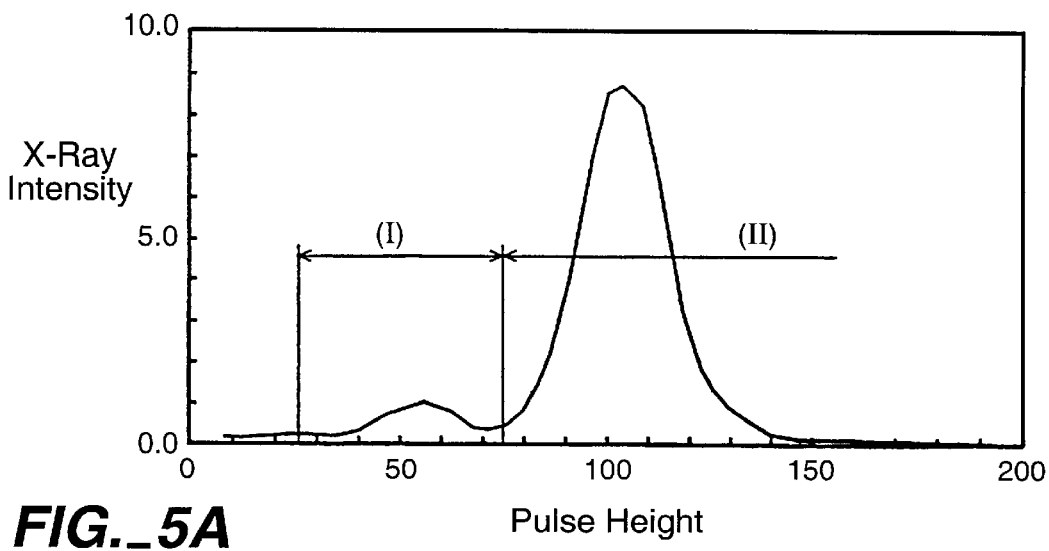
FIG._5A
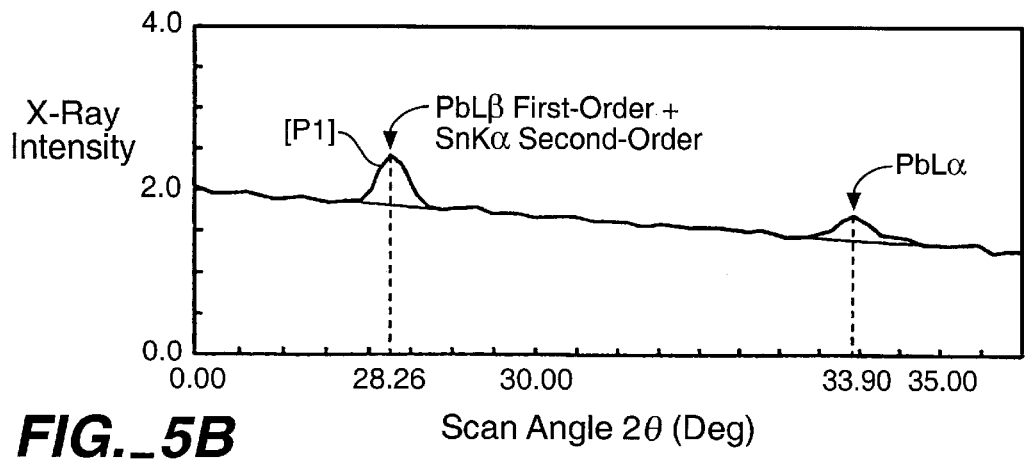
FIG._5B
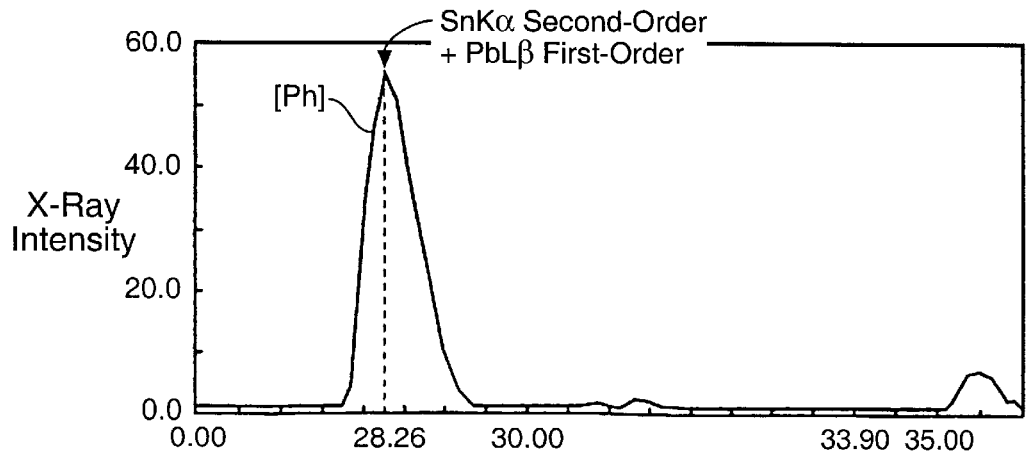
FIG._5C

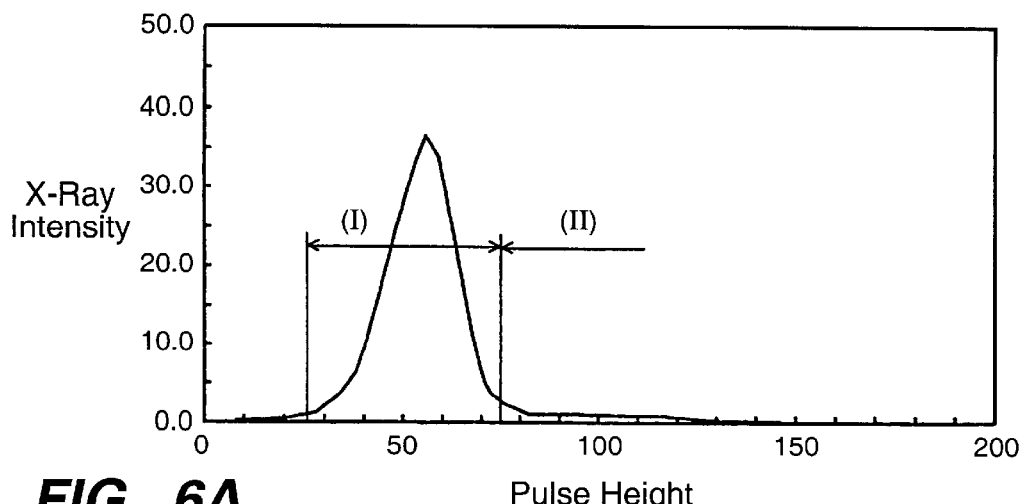
*FIG._6A*
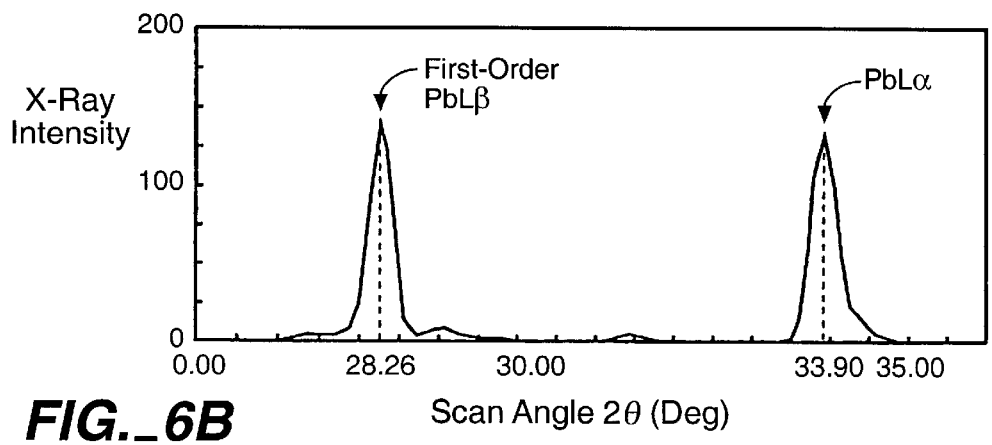
*FIG._6B*
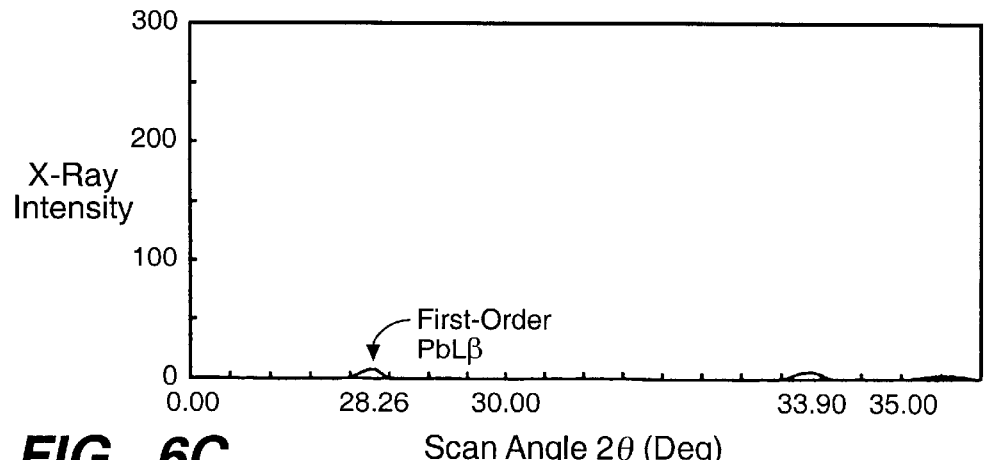
*FIG._6C*

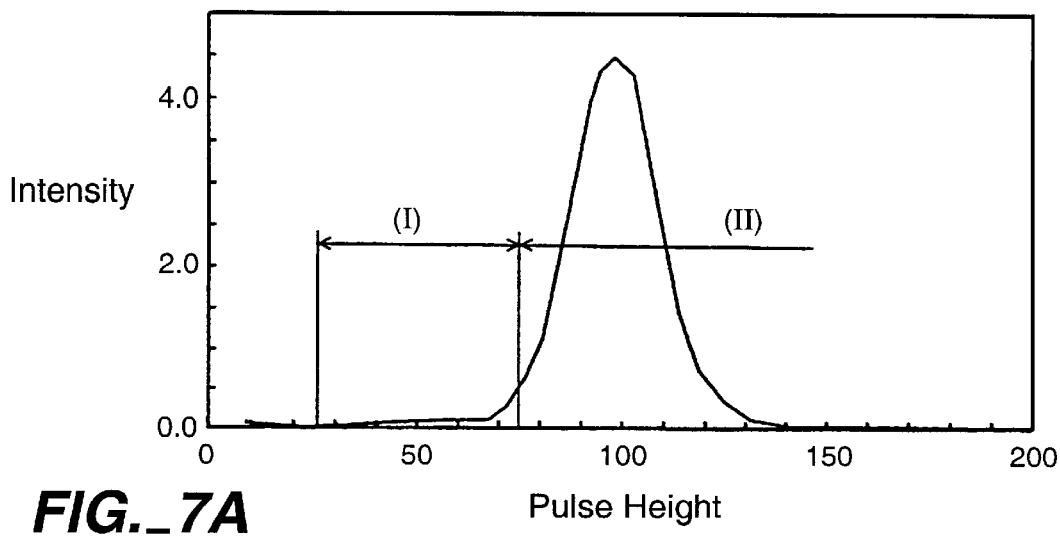
FIG._7A
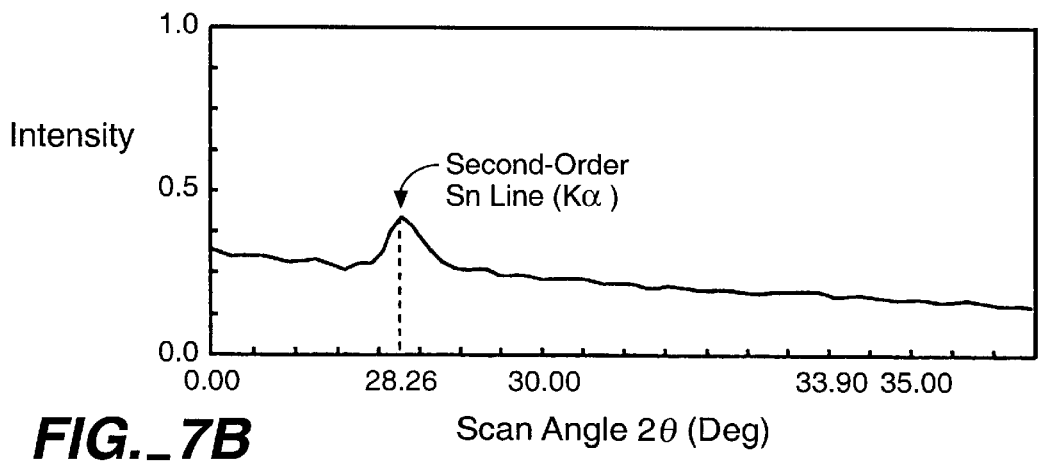
FIG._7B
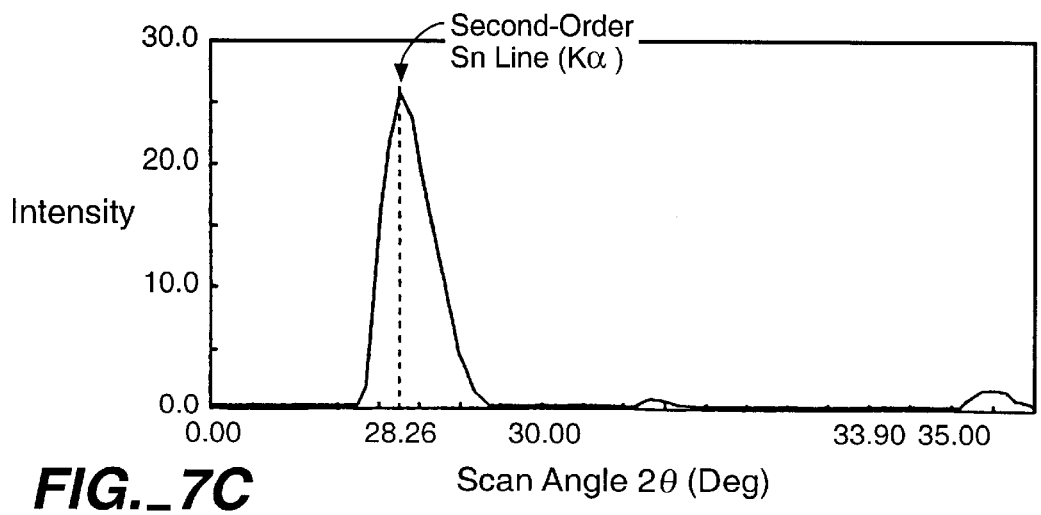
FIG._7C

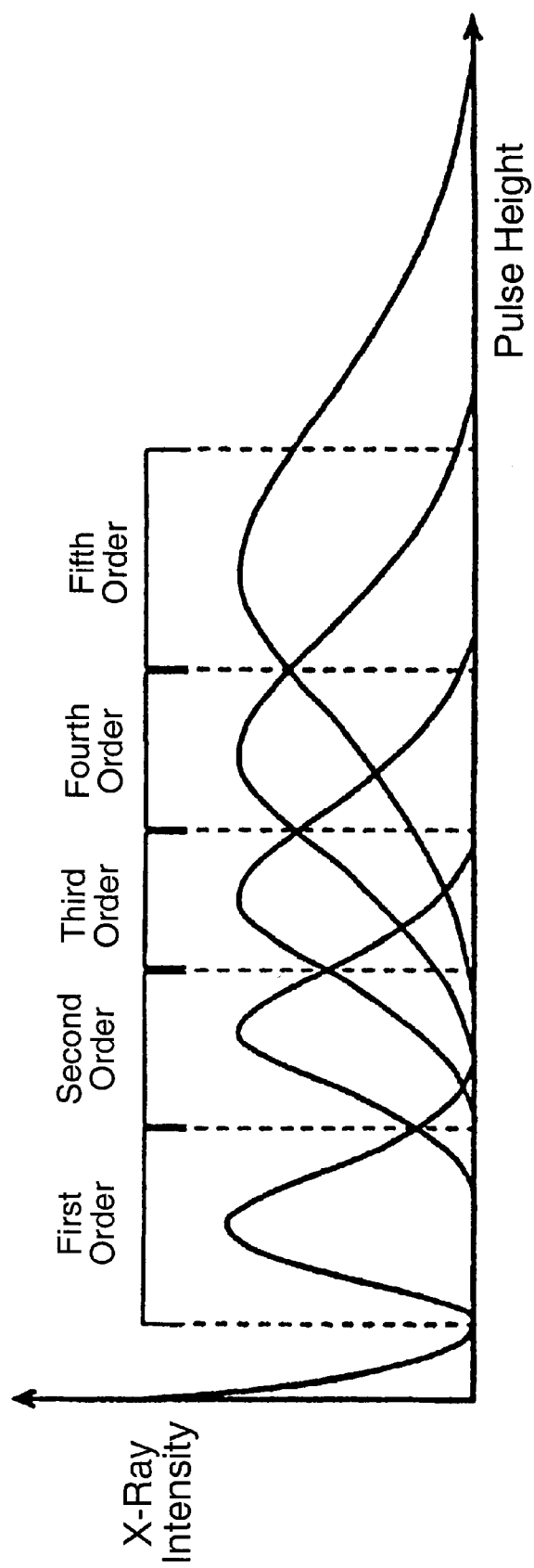
FIG._8

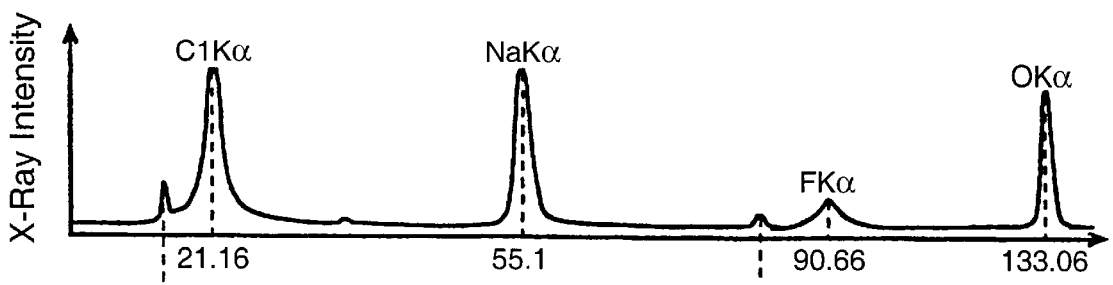
FIG._9A
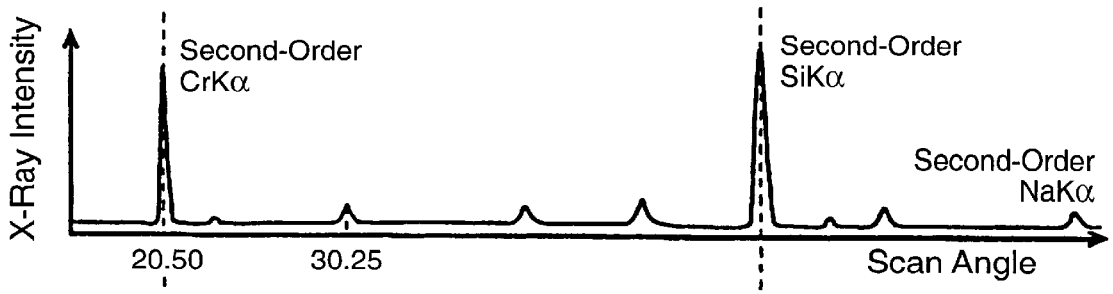
FIG._9B
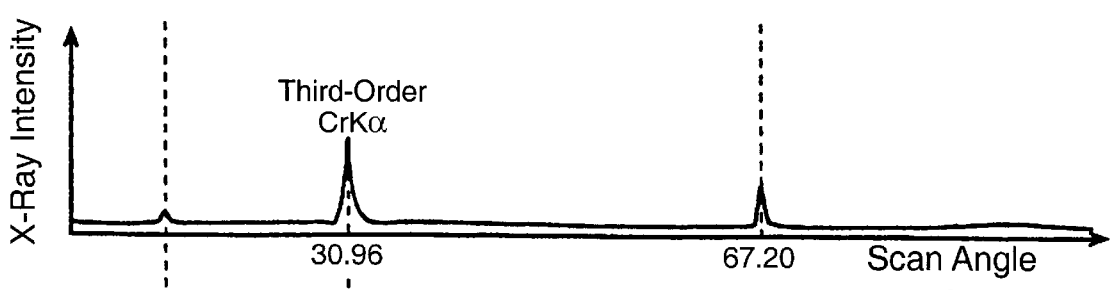
FIG._9C
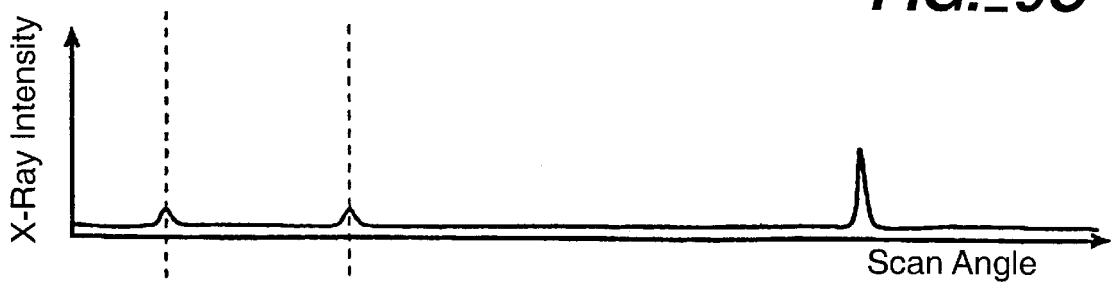
FIG._9D
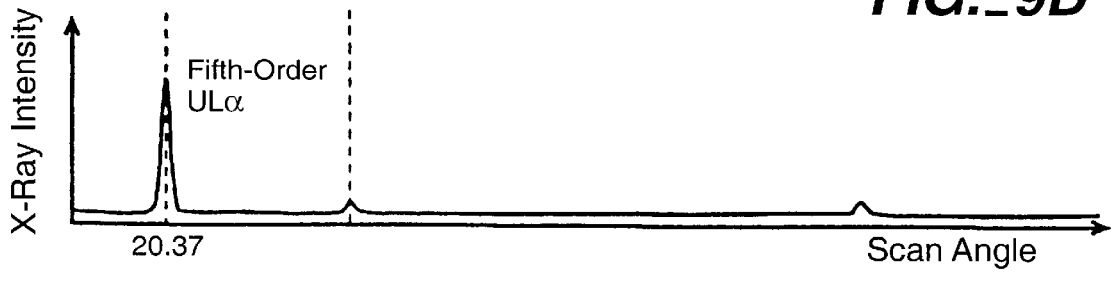
FIG._9E

FLUORESCENT X-RAY ANALYZER

BACKGROUND OF THE INVENTION

This invention relates to a fluorescent x-ray analyzer and more particularly to a fluorescent x-ray analyzer of the wavelength dispersion (WD) type.

A WD type fluorescent x-ray analyzer uses a dispersing crystal to disperse fluorescent x-rays generated by a sample irradiated by x-rays and to introduce diffracted x-rays having a specified wavelength into a detector. For the purpose of wavelength scan, the crystal and the detector are rotated while maintaining a specified angular relationship between them. Explained more in detail, the crystal and the detector are rotated so as to satisfy the Bragg condition given by:

$$2d \sin \theta = n\lambda \quad (1)$$

where d is the lattice interval of the crystal, $2\theta$ is the angle of diffraction, $\lambda$ is the wavelength of the incident fluorescent x-rays and n is the order of diffraction. Since the wavelength of the x-rays entering the detector is gradually changed by such a scan, an x-ray spectrum can be generated by using the scanning angle $2\theta$ as the horizontal axis and the x-ray intensity as the vertical axis.

As can be understood from (1), however, it happens sometimes that the first-order diffraction beam of a certain element overlaps more or less at the same angular position of a diffracted x-ray beam of a higher order (that is, the second or higher order) corresponding to another element. In such a situation, since x-ray photons of these mutually overlapping beams have different energies, the detector may use a pulse height analyzer to differentiate between the wave heights of pulse signals by these x-ray photons such that only the pulse signals corresponding to the first-order diffraction beam are counted, thereby eliminating the effects of the higher-order beams and obtaining the x-ray intensity due only to the first-order beam.

Fluorescent x-rays emitted from a single element, however, usually include many characteristic rays having different wavelengths referred, for example, as K$\alpha$ (more strictly speaking, K$\alpha$a and K$\alpha$2), K$\beta$1, K$\beta$2, K$\beta$3, L$\alpha$1, L2$\alpha$, etc., corresponding to the electron transitions related to the generation of fluorescent x-rays. Thus, when a sample containing a plurality of different elements is qualitatively or quantitatively analyzed on the basis of its x-ray spectrum, the analysis is carried out by determining which characteristic x-rays of which element are forming each of the peaks in the x-ray spectrum and obtaining the x-ray intensity from the top of the peak.

Although a range in pulse height for analysis is properly selected by means of a pulse height analyzer, however, a portion of the pulse signals due to higher-order x-rays of elements with high contents in the sample may fall within the range set by the pulse height analyzer for selecting the height of pulse signals due to the first-order beams. If the peaks are identified or the peak intensity of fluorescent x-rays is calculated by using an x-ray spectrum (hereinafter referred to as the "first-order beam profile") produced on the basis of pulse signals selected by such a pulse height analyzer, peaks of higher-order beams of other elements may be near the scan angle of the first-order beam of an element of interest. In such a situation, it is not possible to determine from the obtained peak profile alone which element is represented by a given spectrum.

In view of the above, it has been known to obtain a first-order beam profile over a wide range covering almost all elements, to start the identification process from the peaks of elements with short wavelengths such that higher-order beam lines of the other elements are not likely to overlap, and to continue the process sequentially with peaks corresponding to elements with longer wavelengths on the basis of the data on the contained elements which have been identified, checking whether there is any overlapping between the first-order beam lines and higher-order beam lines. For analyzing an overlapping region between a peak corresponding to a first-order beam and peaks corresponding to higher-order beams, it has been known to preliminarily obtain the intensity ratio between them for a target element to be analyzed by making measurements on a standard sample and to carry out the analysis by referring to such ratio.

For preparing a first-order beam profile, use must be made of a crystal with lattice interval such that the condition $2d \sin \theta = \lambda \leq 2d$ is satisfied because n=1 in Formula (1) above. When a measurement is carried out over a large range of elements including both light and heavy elements, therefore, it is impossible to entirely cover such a wide range of wavelengths by using only one kind of crystal. Thus, it has been necessary to prepare a plurality of crystals having different lattice intervals corresponding to different spectral wavelength ranges and to keep replacing one by another of them as measurements are taken by scanning within specified angular ranges between the detector and the crystal. In other words, the apparatus had to be provided with a plurality of crystals and also with a device for exchanging these crystals. As a result, the apparatus could not be made small and its cost could not be reduced. Moreover, since the scanning must be repeated many times within a same range of angles, a long time was required for the measurement.

A further problem with the prior art technology has been that different experimental data are necessary for different elements for the analysis of the peaks. Even for the analysis of one element, different data are necessary, depending on the condition of the analysis such as the kind of the crystal and the slit. Even if measurement are taken under the same conditions, it is necessary to preliminarily prepare a huge amount of data in order to obtain an accurate result. This means that preparations become an extremely burdensome part of an analysis.

SUMMARY OF THE INVENTION

It is therefore an object of this invention, in view of these problems, to provide an improved fluorescent x-ray analyzer capable of correctly distinguish and evaluate the first-order peak of one element and a higher-order peak of another element which are overlapped such that the accuracy in qualitative and quantitative analyses can be improved.

It is another object of this invention to provide such a fluorescent x-ray analyzer capable of reducing the burden on its operator and improving the work efficiency by significantly reducing the amount of measurement data which are required to be preliminarily prepared for carrying out such an evaluation.

It is still another object of this invention to provide such a fluorescent x-ray analyzer capable of completing an analysis in a short time by using a crystal of one kind instead of using one after another of many kinds of crystals during an analysis such that the cost of the analyzer itself can be reduced.

A fluorescent x-ray analyzer embodying this invention may be characterized not only as comprising a light-dispersing crystal and a detector which are rotatable while maintaining a specified angular relationship therebetween such that fluorescent x-rays from a sample are scanned by this detector but also wherein a first-order profile and a higher-order profile showing x-ray intensities against scan angle from detection signals from the detector respectively within a specified lower and higher wave height analyzing range. Data related to ratios between preliminarily measured peak intensities of diffracted beams of first-order and higher-order obtained from a plurality of elements are stored and used to identify peaks in the first-order and higher-order profiles, if there is a possibility of a peak formed by a first-order spectrum of one element and a higher-order spectrum of another element overlapping each other and to determine the nature and extent of contributions to the peaks in the first-order and higher-order profiles from the first-order and higher-order spectra.

Explained more in detail, a prior art peak-identification routine is carried out on the first-order and higher-order profiles to identify each peak. If a higher-order diffracted beam of Element B and the first-order beam of Element A are both considered possibly associated with a certain peak, the ratio of peaks due to the first-order and higher-order beams in the case of Element A alone and that in the case of Element B alone, both stored in the memory, are used to determine if there is any contribution from the first-order or higher-order beam of the other element by comparing the peak intensity which would obtain if there were no contribution from the first-order or higher-order beam of the other element and the actually obtained peak intensity. For example, if a certain peak in the first-order profile may be considered to be contributed both from the first-order and higher-order beams, both are identified as the spectrum for this peak, and if it can be concluded that there is no contribution from the first-order beam, only the higher-order beam is identified with the spectrum for this peak. Since the peak intensity due to the first-order beam of Element A can be obtained by subtracting the contribution from the higher-order beams of Element B from the peak intensity appearing in the first-order profile, this peak intensity value can be used in a quantitative analysis.

Another fluorescent x-ray analyzer embodying this invention may be characterized not only as comprising a light-dispersing crystal which outputs diffracted x-rays satisfying Bragg condition corresponding to a specified range of wavelength when fluorescent x-rays from a sample is made incident thereon, a detector for detecting the diffracted x-rays outputted from the light-dispersing crystal and a mechanism for carrying out a scan by rotating the light-dispersing crystal and the detector while maintaining a specified angular relationship between them but also wherein outputs from the detector are separated into mutually different pulse height analyzing ranges and a plurality of profiles each showing x-ray intensity against the scan angle are produced based on those of the detector outputs corresponding to an corresponding one of the pulse height analyzing ranges and a peak in the first-order profile and another peak in one of the higher-order profiles are identified by analyzing both of these peaks by referencing them with each other.

In this analyzer, a light-dispersing crystal corresponding to a relatively light element corresponding to fluorescent x-rays with a longer wavelength is used. Thus, spectra due to the first-order beams from relatively lighter elements appear on the first-order profile while spectra due to higher-order beams of relatively heavy elements satisfying the Bragg condition of Formula (1) appear in the higher-order profile. These profiles include contributions from spectra of different orders but the peaks can be identified by comparing the peaks appearing in these profiles. In this manner, qualitative and quantitative analyses of even heavier elements, of which the first-order beams would not be within the range of scan angles, can be accomplished.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a schematic block diagram of essential parts of a fluorescent x-ray analyzer embodying this invention;

FIG. 2A is an example of pulse height distribution curve which may be obtained by the fluorescent x-ray analyzer of FIG. 1 and FIG. 2B is a portion of FIG. 2A shown enlarged;

FIGS. 3A and 3B are respectively an example of first-order and higher-order light profile obtained by the fluorescent x-ray analyzer of FIG. 1;

FIG. 4 is a flow chart of a routine for data analysis according to this invention;

FIGS. 5A, 5B and 5C are graphs showing measured data obtained with a sample of copper alloy containing lead and tin;

FIGS. 6A, 6B and 6C are graphs showing measured data obtained with a standard sample containing lead but not containing tin;

FIGS. 7A, 7B and 7C are graphs showing measured data obtained with a standard sample containing tin but not containing lead;

FIG. 8 is an example of pulse height distribution curve obtained by another fluorescent x-ray analyzer embodying this invention; and FIGS. 9A, 9B, 9C, 9D and 9E are graphs showing an example of the first-order and higher-order profiles obtained by the same fluorescent x-ray analyzer used for FIG. 8.

DETAILED DESCRIPTION OF THE INVENTION

The invention is described next by way of an example with reference to FIG. 1 wherein numeral 1 indicates an x-ray tube serving as an x-ray source. The fluorescent x-rays generated by a sample 2 irradiated by the primary x-ray beam from this x-ray tube 1 are introduced into an goniometer 3, at the center of which is a light-dispersing crystal 4 for dispersing the fluorescent x-rays according to the wavelength. The diffracted x-ray light dispersed by this crystal 4 is received by a detector 5 disposed on the circumference of the goniometer 3. The crystal 4 and the detector 5 are arranged so as to rotate by angles θ and 2θ (as shown by arrows) under the control of a control unit 10, or so as to rotate the detector 5 by twice the angle by which the crystal 4 is rotated, such that the Bragg condition given by (1) remains satisfied. As the crystal 4 and the detector 5 are thus rotated, the control unit 10 transmits the scan angle 2θ to a data processor 9. Soller slits 11 are provided both on the entrance and exit sides of the crystal 4 so as to limit the width of the x-ray light flux.

The detector 5 may comprise a scintillation counter tube adapted to receive x-ray photons and to generate a pulse signal with height corresponding to the energy of each of the received x-ray photons. After such a pulse signal is amplified by an amplifier 6, it is inputted in parallel to a first pulse height analyzer 7a and a second pulse height analyzer 7b each adapted to output only those of the inputted pulse signals which are within a preliminarily specified range of analysis. The range of analysis (Range I) for the first pulse height analyzer 7a is defined such that first-order light can be effectively taken in. The range of analysis (Range II) for the second pulse height analyzer 7b is defined such that higher-order light (the second order and higher) with higher pulse height than the pulse signal corresponding to the first-order light is effectively taken in. The pulse signals outputted from these pulse height analyzers 7a and 7b are counted respectively by a first counter 8a and a second counter 8b, and values corresponding to the numbers of pulse signals received thereby per unit time are transmitted to the data processor 9. The data processor 9 may comprise a personal computer of an ordinary kind for carrying out various data analyses as will be described below according to specified algorisms.

FIG. 2A shows an example of pulse height distribution curve representing the relationship between the pulse wave height and x-ray intensity received by the detector 5. A portion of FIG. 2A indicated by a circle C therein is enlarged and shown in FIG. 2B. The vertical axis therein indicates the x-ray intensity corresponding to the pulse numbers counted by the first and second counters 8a and 8b. FIGS. 3A and 3B are respectively an example of the first-order and higher-order light profile generated by the data processor 9 based on the signals obtained by the first and second counters 8a and 8b as the crystal 4 and the detector 5 are rotated within a specified angular range of scan.

FIGS. 2A and 2B show that the pulse height distribution curves due to the first-order light and the higher-order light overlap each other. For this reason, although the ranges are optimally specified for the first and second pulse height analyzers 7a and 7b, it is inevitable that each of the profiles includes some of the signals which should correctly be recorded in the other of the profiles. Since the x-ray intensity is simply plotted along the scan angle 2θ, it is not possible even to determine whether or not such an overlapping exists if, for example, the first-order peak (P1) for element A and a higher-order peak (Ph) for element B appear at the same angle or very close to each other, as shown in FIGS. 3A and 3B.

In view of this problem, the data processor 9 of the fluorescent x-ray analyzer of this invention carries out a special peak-identification routine after a first-order profile and a higher-order profile have been produced. This routine is described next with reference to the flow chart of FIG. 4.

Firstly, an ordinary peak-identification process is carried out on the first-order profile such as shown in FIG. 3A, that is, a smoothing process for eliminating statistical errors from the profile waveform and a noise-removal process for eliminating the background noise included in the measured data and thereafter peaks are detected. A peak search program is then carried out for calculating the position (scan angle 2θ) of each peak, the intensity at the peak top and the background intensity, and the identity of the corresponding element, the name of the spectral line (such as Kα and Kβ) and the order of diffraction are guessed for each of the detected peaks by referencing preliminarily stored wavelength table and intensity ratio table (Step S1). If there is a peak (say, P1) appearing nearly at the position of the first-order diffraction of the characteristic x-rays of Element A and the second-order diffraction of the characteristic x-rays of Element B (different from Element A), they are both identified as "candidates" (Step S2).

Next, a similar process is carried out on a higher-order profile as shown in FIG. 3B and the identity of the corresponding element, the name of the spectral line and the order of diffraction are guessed (Step S3). If there is a peak (say, Ph) appearing nearly at the position of a higher-order diffraction of the characteristic x-rays of Element B and the first-order diffraction of the characteristic x-rays of Element A, they are both identified as "candidates" (Step S4).

Next, the portion of the peak intensity Ph in the higher-order profile contributed from the first-order line is subtracted (Step S5). For this, use is made of the ratio PhA/P1A between the peak intensities P1A of the first-order line and PhA of the higher-order lines obtained preliminarily from a measurement on a standard sample containing Element A but not Element B, and the calculation is carried out by estimating the portion of the peak Ph contributed from the higher-order lines to be given as follows:

$$Ph'=Ph-P1(PhA/P1A). \quad (2)$$

Since the portion of the first-order peak P1 contributed from higher-order lines may be considered extremely small, it may be guessed that $Ph \leq P1(PhA/P1A)$.

Thus, if Ph' is equal to or less than zero (YES in Step S6), it is concluded that there is no contribution to the peak Ph from higher-order lines, or that the peak Ph is contributed only from the first-order line of Element A (Step S7). In this case, it is concluded that there is no Element B included and that both peaks P1 and Ph correspond to the first-order line of Element A (Step S8). For a quantitative analysis of Element A, the peak intensity P1 is used as is (Step S9).

If Ph' is not less than zero (NO in Step S6), it is concluded that the peak Ph includes a contribution from a higher-order line of a different element (Step S10). In this situation, the higher-order line of Element B earlier identified as a candidate, is identified as the spectral line of peak Ph (Step S11).

Next, the portion of the peak intensity P1 corresponding to the peak P1 in the first-order profile contributed from the first-order line is subtracted (Step S12). For this, use is made of the ratio P1B/PhB between the peak intensities PhB of the higher-order line and P1B of the first-order line obtained preliminarily from a measurement on another standard sample containing Element B but not Element A, and the calculation is carried out by estimating the portion of the peak P1 contributed from the first-order line to be given as follows:

$$P1'=P1-Ph'(P1B/PhB). \quad (3)$$

If the peak P1 does not include any contribution from the first-order line of Element A, it may be considered that $P1 \leq Ph'(P1B/PhB)$. Thus, if P1' is equal to or less than zero (YES in Step S13), it is concluded that the peak P1 is contributed only from the higher-order line of Element B (Step S14). Since it may be concluded in this situation that Element A is not contained at all, the peaks P1 and Ph are both identified as higher-order spectral lines of Element B (Step S15).

If P1' is larger than zero (NO in Step S13), it is concluded that the peak P1 includes contributions both from the peak intensity P1' due to the first-order line of Element A and the peak intensity Ph'(P1B/PhB) of the higher-order line of Element B (Step S16) and the peaks P1 and hence the peaks P1 and Ph are identified as the first-order spectral line of Element A and a higher-order spectral line of Element B, respectively (Step S17). For a quantitative analysis of Element A, the peak intensity P1' according to the first-order line obtained by Formula (3) given above is used (Step S18).

Thus, peaks where first-order and higher-order lines of different elements are suspected to be overlapping can be correctly identified, and the x-ray intensity corresponding to the first-order line of an element can be accurately calculated by eliminated the contribution from the higher-order line.

The routine described above will be explained next by way of an example of actual experiment where the sample 2 was a copper alloy containing Pb by 0.15% and tin by 9.02%. The light-dispersing crystal 4 was that of LiF (surface of diffraction: 200), and the detector 5 was a scintillation counter. This example was chosen because the first-order L$\beta$ line of Pb and the second-order K$\alpha$ line of Sn both have a peak near the scan angle 2$\theta$ of the goniometer 3 near 28.2°. FIGS. 5A, 5B and 5C show the measured data obtained with this sample, FIG. 5A showing the pulse height distribution curve at scan angle 28.26°, FIG. 5B showing the first-order profile and FIG. 5C showing the higher-order profile. FIGS. 6A, 6B and 6C are similar to FIGS. 5A, 5B and 5C except where a lead plate containing lead by 99.9% was used as the sample serving as a standard sample containing lead but not tin. FIGS., 7B and 7C are similar to FIGS. 5A, 5B and 5C except where a tin plate containing tin by 99.9% serving as another standard sample containing tin but not lead is used.

It is to be noted that both the first-order and higher-order profiles shown in FIGS. 5B and 5C include a peak near the scan angle of 28.26° and that the first-order L$\beta$ line of lead and the second-order K$\alpha$ line of tin are superposed in both these peaks. It is not possible from these data alone, however, to know how they are superposed or to separate their contributions. Thus, the data processor 9 carries out the routine described above to analyze the data, firstly identifying the first-order L$\beta$ line of lead and the second-order K$\alpha$ line of tin as the "candidates" for both of the peaks at 28.26° in the first-order and higher-order profiles of FIGS. 5B and 5C. Next, Ph' is calculated by Formula (2) for the peak Ph in the higher-order profile of FIG. 5C. In this calculation, use is made of the intensities of the peaks at 28.26° in the first-order and higher-order profiles of FIGS. 6B and 6C for lead. In the present case, Ph'=53.3 −0.647 ×(4.91/142.9)= 53.28 which is clearly larger than zero, and it is hence concluded that the peak Ph of FIG. 5C includes a contribution from the second-order K$\alpha$ line of tin. Similarly, P1' is calculated by Formula (3) for the peak P1 in the first-order profile of FIG. 5B by making use of the intensities of the peaks at 28.26° in the first-order and higher-order profiles of FIG. 7B and 7C for tin. In the present case, P1'=0.647 −53.28 ×(0.172/25.24)=0.284 which, too, is sufficiently larger than zero, and it is hence concluded that both the first-order L$\beta$ line of lead and the second-order K$\alpha$ line are contributing to the peak P1 of FIG. 5B. At the sane time, the peak intensity of the first-order L$\beta$ line of lead in the peak P1 is obtained as 0.284.

The peak appearing near the scan angle of 33.9° in the first-order profile shown in FIG. 5B is the L$\alpha$ line of lead. The ratio between the peak intensity of this line and that of the first-order L$\beta$ line calculated above is 0.306/0.286 =1/0.928, which is substantially equal to the ratio 5.41/4.91 =1.0/0.908 between lines L$\alpha$ and L$\beta$ of lead obtained from a lead plate. This proves that the effects of the superposing second-order K$\alpha$ line of tin obtained above have been correctly separated away and the peak intensity of the first-order L$\beta$ line of lead has been obtained with a high degree of accuracy.

In the example described above, a sample not containing arsenic was used and the ratio between lines L$\alpha$ and L$\beta$ of lead agreed substantially with the measurements on a lead plate. In the case of a sample containing both lead and arsenic, however, there is a peak corresponding to line L$\alpha$ of arsenic near the scan angle of 33.9° and hence the ratio in peak intensity between the peaks at 28.2° and 33.9° becomes larger. Thus, if the intensity of the L$\beta$ line of lead can be obtained accurately as described above, the overlapping of the K$\alpha$ line of arsenic with the L$\alpha$ line of lead can be correctly determined on this basis. In this situation, quantitative analysis of lead cannot be made from the intensity of the L$\alpha$ line of lead, but the L$\beta$ line of lead may be used for an accurate analysis even in the presence of tin.

In summary, the peak intensity of a higher-order line can be made use of in a quantitative analysis if the overlapping of first-order and higher-order lines in peaks appearing in the first-order and higher-order profiles can be correctly evaluated. In other words, a sample containing both lighter elements and heavier elements, together having first-order diffraction lines over a wide range of wavelengths, can be analyzed by using a peak of a higher-order line (not the first-order line) in the case of a heavier element to make identifications, and the quantitative analysis can be carried out by using its peak intensity.

Next, another fluorescent x-ray analyzer having such a function will be described by way of an example.

Unlike the example of fluorescent x-ray analyzer described above characterized as being adapted to record all higher-order lines in one profile, this analyzer prepares profiles of higher-order lines individually. For this purpose, use is made of a multi-channel pulse height analyzer with pulse height discriminating ranges which is set so as to separate the pulse height value of a pulse signal among different orders. FIG. 8 shows an example of pulse height distribution curves. The pulse height distribution tends to spread more widely for higher orders and the degree of overlapping with the distribution curves of the neighboring orders becomes greater. The multi-channel pulse height analyzer is set such that the heights of pulse signals corresponding to different higher-order lines can be discriminated optimally.

According to one embodiment of this invention, the light-dispersing crystal 4 is thallium hydrogen phthalate (TAP) with lattice interval 2$d$=25.75Å. TAP has conventionally been used for measuring the first-order lines of lighter elements such as oxygen, fluorine, sodium and magnesium. The first-order lines of heavier elements have never been considered, but higher-order lines of heavier elements come within the range of scan. FIGS. 9A, 9B, 9C, 9D and 9E respectively show an example of first-order through fifth-order profiles prepared by the data processor 9 as the crystal 4 and the detector 5 are rotated over a certain range of scan angle.

After such profiles are obtained, the data processor 9 carries out an ordinary peak-identifying routine for each profile, determining candidate spectra for each peak. The spectra thus selected as candidates are referenced together to associate each peak with a spectrum or spectra. For example, when the peak corresponding to the first-order line of a certain element is in the first-order profile, it is determined whether peaks corresponding to the higher-order lines of this element are found in the profiles of the corresponding orders. If they are found in the higher-order profiles, the peak is identified with this element. If there is the possibility that a peak due to the first-order line of a certain element overlaps with another peak of a higher-order line of another element, the overlapping can be investigated as described above to identify the peak with a spectrum or spectra.

After each peak is thus identified with a spectrum or spectra, the peak intensities are calculated and a quantitative analysis is carried out by the so-called fundamental parameter method from the x-ray intensities of each element. An ordinary fundamental parameter method requires intensities and some other equivalent information on all elements contained in a sample but the method of this invention requires only measured data by using a crystal of only one kind to obtain such information.

The invention was described above by way of only a limited number of examples but these examples are not intended to limit the scope of the invention. Many modifications and variations are possible within the scope of the invention. For example, the functions of the two pulse height analyzers 7a and 7b may be combined into one pulse height analyzer adapted to set selectably either of the two discriminating ranges (Ranges I and II). The scanning is carried out at least twice and the first-order profile and the higher-order profile are produced sequentially, not in parallel.

Advantages to be gained by the present invention include the following.

Firstly, the overlapping condition between a peak in a first-order line and another in a higher-order line can be determined accurately, including the degree of overlapping. Thus, an analyzer according to this invention can be used dependably for both qualitative and quantitative analyses.

Secondly, since the degree to which a higher-order line contributes to a first-order profile or that to which a first-order line contributes to a higher-order profile, which may be used for the evaluation of the overlapping of spectra, depends only on the kind of the detector and the wavelength (energy) of the element, but not on the kind of the crystal used for dispersion or the slit width, the number of conditions to be varied when measured data are collected can be reduced.

Thirdly, since peaks appearing not only in the first-order profile but also in higher-order profiles can be used for qualitative and quantitative analyses, it is not necessary any more to prepare a first-order profile over a wide range of wavelengths covering both lighter and heavier elements. Thus, it is not necessary to use a plurality of light-dispersing crystals. One has only to make measurements over a range of angles which are possible with one crystal. As a result, there is no need to repeat measurements by using many different crystals. The time required for the measurements can thus be significantly reduced and the cost of the analyzer itself can also be reduced.

What is claimed is:

1. A fluorescent x-ray analyzer comprising:

a light-dispersing crystal and a detector which are rotatable while maintaining a specified angular relationship therebetween such that fluorescent x-rays from a sample are scanned by said detector;

first-order profile producing means for producing a first-order profile showing x-ray intensities against scan angle from detection signals from said detector within a specified pulse height discriminating range of wavelength;

higher-order profile producing means for producing a higher-order profile showing x-ray intensities against scan angle from detection signals from said detector within a higher pulse height discriminating range of wavelength which is higher than said specified pulse height discriminating range;

memory means for storing data related to ratios between preliminarily measured peak intensities of first-order and higher-order beams of a plurality of elements; and data processing means for identifying peaks in said first-order profile and said higher-order profile, if there is a possibility of a peak formed by a first-order spectrum of one element and a higher-order spectrum of another element overlapping each other, by using data stored in said memory means and thereby determining contributions to said peaks in said first-order profile and said higher-order peaks from said first-order spectrum and said higher-order spectrum.

2. The fluorescent x-ray analyzer of claim 1 wherein said light-dispersing crystal is positioned so as to output diffracted x-rays satisfying Bragg condition corresponding to a specified range of wavelength when fluorescent x-rays from a sample is made incident thereon.

3. The fluorescent x-ray analyzer of claim 1 wherein said first-order profile producing means serves to determine said specified pulse height discriminating range so as to effectively discriminate diffracted x-rays of first order from said light-dispersing crystal and includes a first counter for counting pulse signals from said detector corresponding to said specified pulse height discriminating range, wherein said higher-order profile producing means serves to determine said higher pulse height discriminating range so as to effectively discriminate diffracted x-rays of second and higher orders from said light-dispersing crystal and includes a second counter for counting pulse signals from said detector corresponding to said higher pulse height discriminating range, and wherein said first-order profile and said higher-order profile are produced concurrently as said light-dispersing crystal and said detector are rotated.

4. A fluorescent x-ray analyzer comprising:

a light-dispersing crystal which outputs diffracted x-rays satisfying Bragg condition corresponding to a specified range of wavelength when fluorescent x-rays from a sample is made incident thereon;

a detector for detecting said diffracted x-rays outputted from said light-dispersing crystal;

scanning means for carrying out a scan by rotating said light-dispersing crystal and said detector while maintaining a specified angular relationship therebetween;

profile producing means for separating outputs from said detector into mutually different pulse height discriminating ranges and producing a plurality of profiles each showing x-ray intensity against angle of said scan based on those of said outputs from said detector associated with a corresponding one of said pulse height discriminating ranges, said profiles including a first-order profile corresponding to the lowest of said pulse height discriminating ranges and higher-profiles corresponding to higher pulse height discriminating ranges than the lowest pulse height discriminating range; and data processing means for identifying a specified first peak in said first profile and a specified second peak in one of said higher profiles by analyzing both said first peak and said second peak by referencing each other.

* * * * *